United States Patent
Sato et al.

(10) Patent No.: US 7,807,428 B2
(45) Date of Patent: Oct. 5, 2010

(54) METHOD FOR PRODUCING AN IMMOBILIZED ENZYME FOR HYDROLYZING FATS AND OILS

(75) Inventors: Manabu Sato, Kamisu (JP); Kazuhiro Onozuka, Kamisu (JP); Takaaki Watanabe, Kamisu (JP); Hiroyuki Konishi, Kamisu (JP)

(73) Assignee: Kao Corporation, Tokyo (JP)

( * ) Notice: Subject to any disclaimer, the term of this patent is extended or adjusted under 35 U.S.C. 154(b) by 327 days.

(21) Appl. No.: 11/270,497

(22) Filed: Nov. 10, 2005

(65) Prior Publication Data
US 2006/0121584 A1 Jun. 8, 2006

(30) Foreign Application Priority Data
Nov. 12, 2004 (JP) ............................. 2004-329779

(51) Int. Cl.
C12N 11/00 (2006.01)
C12N 11/14 (2006.01)
C12N 11/02 (2006.01)
C12N 11/10 (2006.01)
C12N 11/08 (2006.01)
C12P 7/64 (2006.01)

(52) U.S. Cl. ....................... 435/174; 435/134; 435/176; 435/177; 435/178; 435/180

(58) Field of Classification Search ........................ None
See application file for complete search history.

(56) References Cited

U.S. PATENT DOCUMENTS

| 5,128,251 A * | 7/1992 | Yokomichi et al. .......... 435/134 |
| 5,342,768 A * | 8/1994 | Pedersen et al. ............ 435/134 |
| 2005/0019883 A1 | 1/2005 | Sato et al. |

FOREIGN PATENT DOCUMENTS

| EP | 0 294 520 A1 | 12/1988 |
| EP | 1 008 647 A2 | 6/2000 |
| EP | 1 378 568 A1 | 1/2004 |
| JP | 9-56379 | 3/1997 |
| JP | 2000-253874 | 9/2000 |
| JP | 2004-081200 A | 3/2004 |

OTHER PUBLICATIONS

U.S. Appl. No. 11/668,182, filed Jan. 29, 2007, Sato, et al.
Miroslawa Szczesna-Antczak, et al., "Catalytic properties of membrane-bound *Mucor* lipase immobilized in a hydrophilic carrier", Elsevier, Journal of Molecular Catalysis B: Enzymatic, vol. 19-20, XP-002357498, Dec. 2, 2002, pp. 261-268.

* cited by examiner

*Primary Examiner*—David M Naff
(74) *Attorney, Agent, or Firm*—Oblon, Spivak, McClelland, Maier & Neustadt, L.L.P.

(57) ABSTRACT

A method for producing an immobilized enzyme which includes the steps of immobilizing an enzyme used for hydrolyzing fats and oils on a immobilization carrier by adsorption, bringing the immobilized enzyme into contact with an organic solvent in which fat-soluble fatty acids or the derivatives thereof have been dissolved, and adjusting the moisture content of the immobilized enzyme from 1 to 20% by weight based on the weight of the carrier.

1 Claim, No Drawings

METHOD FOR PRODUCING AN IMMOBILIZED ENZYME FOR HYDROLYZING FATS AND OILS

FIELD OF THE INVENTION

The present invention relates to a method for producing immobilized enzyme to be used as a catalyst of hydrolysis reaction of fats and oils (mono-, di-, or triglyceride), esterification reaction of fatty acid with an alcohol, or transesterification reaction of fats and oils.

BACKGROUND OF THE INVENTION

The use of an enzyme for hydrolyzing fats and oils has been increased in many cases of the production of hydrolysates of fats and oils (mono-, di-, or triglyceride), or the production of esters from fatty acids and alcohols by the reverse reaction of hydrolysis, and the production of new glycerides by exchanging acyl group of the fats and oils. Especially in the case of producing fats and oils with functionality, a lipase having a position specificity has been used frequently. And, in order to recover and reuse the lipase enzyme, an immobilized enzyme can be used.

Many of the immobilized enzymes which are available at present are offered in a dried form, taking into consideration the inhibition of an enzyme from deactivation during storage and proper handling. However, deactivation of an immobilized enzyme is liable to occur at a step where the immobilized enzyme is dried under reduced pressure, in a vacuum or by heating, and the maximum activity of the immobilized enzyme is not achieved in many cases. Meanwhile, a method of water removal by treating the enzyme with organic solvent has been known (JP-A-2000-253874), but all the same, the maximum activity of the enzyme is not achieved against the original activity of the adsorbed enzyme.

On the other hand, a method for increasing the recovery of enzyme activity has been proposed, wherein the drying of the immobilized enzyme is carried out by contacting with fatty acid derivatives (JP-A-1987-134090). In addition, a method for producing an immobilized enzyme for esterification reaction showing high activity has been published (JP-A-2000-166552, JP-A-2004-81200), wherein the deactivation of the enzyme is prevented by controlling the moisture content of the immobilized enzyme by bringing the immobilized enzyme into contact with a fatty acid glyceride, or dehydrating after bringing the immobilized enzyme into contact with the above glyceride.

SUMMARY OF THE INVENTION

The present invention provides a method for producing an immobilized enzyme which includes the steps of immobilizing an enzyme used for hydrolyzing fats and oils on a immobilization carrier by adsorption, bringing the immobilized enzyme into contact with an organic solvent in which fat-soluble fatty acids or the derivatives thereof have been dissolved, and adjusting the moisture content of the immobilized enzyme from 1 to 20% by weight based on the weight of the carrier.

DETAILED DESCRIPTION OF THE INVENTION

The above described method for drying the immobilized enzyme by contacting with fatty acid derivatives is inefficient because the procedure has to be carried out slowly, and also impractical because the establishment of the drying condition or the like are complicated and expensive equipments are needed.

Also, the immobilized enzyme prepared by method of conducting dehydration of the enzyme under contacting with the glycerides or the like after the above described enzyme is immobilized by adsorption to the immobilization carrier, has a problem with respect to its inconvenient form for handling because the enzyme is infiltrated by glycerides of the fatty acid or the like.

The present inventors have found that, after the enzyme is immobilized by adsorption to an immobilization carrier, the moisture content of immobilized enzyme can be controlled with maintaining high level of enzyme activity, by contacting the immobilized enzyme with an organic solvent in which fat-soluble fatty acids or the derivatives thereof have been dissolved, and also, the difficulty of handling can be improved at the same time because the glycerides of fatty acids and the like can sufficiently be decreased in the immobilized enzyme.

The immobilization carrier for the immobilized enzyme to be used in the present invention includes inorganic carriers such as celite, diatomaceous earth, kaolinite, silica gel, molecular sieves, porous glass, activated carbon, calcium carbonate and ceramics, and organic polymers such as ceramics powder, polyvinyl alcohol, polypropylene, chitosan, ion-exchange resins, hydrophobic adsorption resins, chelating resins and synthetic adsorptive resins, and ion-exchange resins are preferable.

As to the ion-exchange resins, porous anion-exchange resins are preferable. Such a porous carrier has a large surface area, whereby the adsorption of a large amount of enzyme may be attained. The particle size of the resin is preferably from 100 to 1000 μm in diameter, and its pore size is preferably from 10 to 150 nm. The material for the immobilization carrier includes phenol-formaldehyde, polystyrene, acryl amide, divinylbenzene and the like, and among them, the phenol formaldehyde resin (for example, Duolite A-568, produced by Rohm and Haas Co.) is more preferable.

As to the enzyme for hydrolyzing fats and oils to be used in the present invention, a lipase is preferable. The commercially available lipases derived from microorganisms as well as those derived from animals or plants may be used. The lipase derived from microorganisms includes the enzymes produced by the microorganisms belonging to for example the genus of *Rizopus, Aspergillus, Mucor, Pseudomonas, Geotrichum, Penicillium*, and *Candida*. Especially when the functional fats and oils are aimed to be produced, use of a lipase having a position specificity which has ability to generate a binding selectively on the desired position of the glycerol, such as 1, 3-position-selective lipase derived from the microorganisms belonging to the genus of *Rizopus, Aspergillus, Mucor, Pseudomonas, Geotrichum*, or *Penicillium*, is more preferable.

In immobilization of the enzyme, the enzyme may be adsorbed directly on the carrier, or, the carrier may be treated in advance with the fat-soluble fatty acids or the derivatives thereof before adsorbing thereon the enzymes in order to obtain such adsorption state that a high activity is revealed. The fat-soluble fatty acid to be used in the present invention includes saturated or unsaturated fatty acids with 8 to 18 carbon atoms with linear or branched chain, or the fatty acids having displaced hydroxyl group. Such fatty acids include, for example, capric acid, lauric acid, myristic acid, oleic acid, linoleic acid, α-linolenic acid, recinoleic acid, and isostearic acid. In addition, the derivatives of the fatty acids include the esters of the above fatty acids with monohydric or polyhydric alcohol, phospholipids, and the addition derivatives of these esters with ethylene oxide. The fatty acid derivatives include, for example methyl ester, ethyl ester, monoglyceride, diglyceride, their addition compounds with ethylene oxide, polyglycerol ester, sorbitan ester, and sucrose ester of the above described fatty acids. Two or more of these fat-soluble fatty acids or the derivatives thereof may be used in combination.

The contact of these fat-soluble fatty acids or the derivatives thereof with the carrier may be performed by adding these materials directly in water or organic solvent, however, to attain a good dispersibility the fat-soluble fatty acids or the derivatives thereof may be dispersed and dissolved in an organic solvent beforehand and then added to the carrier dispersed in water. Such organic solvent includes chloroform, hexane, ethanol and the like. The amount of the fat-soluble fatty acids or the derivative thereof to be used is preferably from 1 to 500% by weight, and more preferably from 10 to 200% by weight based on the weight of the carrier. The contact temperature is preferably from 0 to 100° C., and more preferably from 20 to 60° C. The contact time is preferably from about 5 minutes to about 5 hours. The carrier processed by the above described treatment is recovered by filtration, and may be dried. The drying temperature is preferably from room temperature to 100° C., and may be dried under reduced pressure.

The temperature of immobilization reaction can be determined based on the characteristics of the enzyme, however, the temperature from 0 to 60° C., at which deactivation of the enzyme does not occur, is preferable and the temperature from 5 to 40° C. is more preferable. The pH of the enzyme solution to be used for immobilization process may be within the range at which deactivation of the enzyme does not occur and it may be determined based on the characteristics of the enzyme as well; however, pH from 3 to 9 is preferable. To maintain this pH, a buffer solution is used, which includes acetate buffer solution, phosphate buffer solution, and Tris-HCl buffer solution.

The concentration of the enzyme in the above described solution is desirably lower than the saturation solubility while sufficient concentration from the view point of maintaining immobilization efficiency. Further, if needed, a supernatant solution after insoluble substance in the enzyme solution is removed by centrifugal separation, or the solution purified by ultra filtration or the like may also be used as an enzyme solution. The amount of the enzyme to be used is preferably from 5 to 1000% by weight, and more preferably from 10 to 500% by weight based on the weight of the carrier.

After immobilization of the enzyme, the moisture content in the immobilized enzyme is controlled by means of contacting the enzyme with an organic solvent in which fat-soluble fatty acids or the derivatives thereof have been dissolved. The remaining moisture content is controlled to be from 1 to 20% by weight based on the weight of the carrier, and that from 2 to 15% by weight is preferable, and that from 3 to 10% by weight is more preferable.

The preferable fat-soluble fatty acids to be used for the above described treatment are those derived from vegetal liquid fat such as rapeseed oil, soybean oil and sunflower oil, or fish oil such as sardine oil, tuna oil and bonito oil, and the derivatives thereof include these fats and oils themselves and lower alcohol esters derived from these fats and oils. Two or more kinds of these fatty acids may be used in combination. In addition, regarding the fat-soluble fatty acids or the derivatives thereof to be used in this process, it is preferable to select from oil phase substrates, its hydrolysates, or its low alcohol esters in the actual hydrolysis reaction, esterification reaction, or transesterification reaction catalyzed by the immobilized enzyme prepared according to the present invention.

The amount of fat-soluble fatty acids and the derivatives thereof to be used in this process is preferably from 1 to 500% by weight, and more preferably from 10 to 200% by weight based on the weight of the carrier from the view point of getting sufficient contact with the immobilized enzyme and avoiding waste of excessive use.

The organic solvent to be used for the above described treatment includes acetone, ethanol, and a mixture thereof. Among these organic solvent, from the view point of prevention of the deactivation of the enzyme and volatile characteristics, acetone or a mixture of acetone and other organic solvent is preferable.

The amount of organic solvent to be used is preferably from 100 to 3000% by weight, and more preferably from 200 to 2000% by weight based on the weight of carrier from the view point of getting sufficient contact with the immobilized enzyme and avoiding waste of excessive use.

The contact of the immobilized enzyme with an organic solvent in which fat-soluble fatty acids or the derivatives thereof have been dissolved may be performed by any type of method selected from soaking, dispersion, stirring, passing the solvent through a column packed with the immobilized enzyme by pumping, and the like. The contact temperature may be the temperature at which the oil phase does not solidify during the contact, and which may be determined optionally according to the properties of the fat-soluble fatty acid or the derivatives thereof and the enzyme, in particular, the temperature from 0 to 40° C. is preferable, and that from 5 to 30° C. is more preferable. The contact time is preferably from 1 to 30 minutes, and that from 3 to 10 minutes is more preferable. If needed, a plural time of treatment may be conducted.

The moisture content of the immobilized enzyme at the time when the enzyme is immobilized by adsorption on the carrier is generally within the range from 120 to 300% by weight based on the weight of the carrier; however the present invention can adjust the moisture content of the immobilized enzyme from 1 to 20% by weight based on the weight of the carrier by contacting with an organic solvent in which fat-soluble fatty acids or the derivatives thereof have been dissolved. By the above described treatment, damages to the enzyme that occurred at the process of forced removal of moisture such as common drying treatment may be minimized, and thus the immobilized enzyme with high activity may be prepared.

After completion of the contact process, the immobilized enzyme is recovered by filtration, as appropriate.

EXAMPLES

Example 1

A 100 g of Duolite A-568 (Rohm and Haas Co.) which was used as a carrier was stirred in 1 L of 0.1 N NaOH solution for one hour. After filtration, it was washed with 1 L of distilled water, and pH was equilibrated with 1 L of 500 mM acetate buffer solution (pH 6). Then, the pH equilibration was repeated twice, each for 2 hours, with 1 L of 50 mM acetate buffer solution (pH 6). After recovery of the carrier by filtration, solvent replacement was carried out using 500 mL of ethanol for 30 minutes. After filtration, the carrier was contacted for 30 minutes with 500 mL of ethanol solution containing 100 g of recinoleic acid. After filtration, solvent replacement by buffer solution was carried out 4 times with each 500 mL of 50 mM acetate buffer solution (pH 6) for 30 minutes. After filtration, adsorption of the enzyme was performed by contacting the carrier with 1000 mL of 3% Lipase F-AP15 (Amano Enzyme Inc.) solution for 2 hours at room temperature. After adsorption the enzyme-adsorbed carrier was recovered by filtration, and washed with 500 mL of 50 mM acetate buffer solution (pH 6) for 30 minutes. After washing, the immobilized enzyme was recovered by filtration.

To this immobilized enzyme, a solution of 100 g of oleic acid dissolved in 500 g of acetone was added, and stirred at 20° C. for 5 minutes, and then the immobilized enzyme was recovered by filtration. At this time, the amount of remaining moisture in the immobilized enzyme was 7.9% by weight based on the weight of the carrier.

Example 2

The immobilized enzyme was prepared and recovered by the same procedure as described in Example 1. To this immobilized enzyme, a solution of 200 g of oleic acid dissolved in 800 g of acetone was added, and stirred at 20° C. for 5 minutes, and then the immobilized enzyme was recovered by filtration. At this time, the amount of remaining moisture in the immobilized enzyme was 6.5% by weight based on the weight of the carrier.

Example 3

The immobilized enzyme was prepared and recovered by the same procedure as described in Example 1. To this immobilized enzyme, a solution of 100 g of rapeseed oil dissolved in 500 g of acetone was added, and stirred at 20° C. for 5 minutes, and then the immobilized enzyme was recovered by filtration. At this time, the amount of remaining moisture in the immobilized enzyme was 7.7% by weight based on the weight of the carrier.

Comparative Example 1

The immobilized enzyme was prepared and recovered by the same procedure as described in Example 1. To this immobilized enzyme, 500 g of acetone was added, and stirred at 20° C. for 5 minutes, and then the immobilized enzyme was recovered by filtration. At this time, the amount of remaining moisture in the immobilized enzyme was 7.2% by weight based on the weight of the carrier.

Comparative Example 2

The immobilized enzyme was prepared and recovered by the same procedure as described in Example 1. To this immobilized enzyme, 1000 g of oleic acid was added, and stirred at 40° C. for 2 hours, and then the immobilized enzyme was recovered by filtration. At this time, the amount of remaining moisture in the immobilized enzyme was 134% by weight based on the weight of the carrier.

Comparative Example 3

The immobilized enzyme was prepared and recovered by the same procedure as described in Example 1. To this immobilized enzyme, 1000 g of rapeseed oil was added, and stirred at 40° C. for 2 hours, and then the immobilized enzyme was recovered by filtration. At this time, the amount of remaining moisture in the immobilized enzyme was 30% by weight based on the weight of the carrier.

Test Example 1

The measurement of the relative activity and the evaluation of the easiness of handling of each immobilized enzyme were carried out according to the procedures described below.

[Measurement of the Relative Enzyme Activity]

4 g of the immobilized enzyme as dry weight was weighed, and put into a 200 mL four-neck flask. 80 g of a mixture of oleic acid and glycerol (oleic acid/glycerol=2.0 by molar ratio) was added into the flask to carry out the esterification reaction under reduced pressure of 400 Pa at 50° C. The reaction mixture was sampled occasionally and the change of the glyceride composition over time was followed up. In addition, the glyceride composition of each sample of reaction mixture was analyzed by gas chromatography after the sample was trimethylsilylated. The activity of the immobilized enzyme was defined as the time taken for coming up the sum of diglyceride (DG) plus triglyceride (TG) to 70% by weight, and represented by a relative value to the activity of Example 1 which was assumed as 100%. The results were shown in Table 1.

[Evaluation of the Easiness of Handling of the Immobilized Enzyme]

The easiness of handling of the immobilized enzyme was evaluated by the passage rate through a sieve.

The sieving test was carried out using about 100 g of the immobilized enzyme as dry weight. Using a standard sieve of 200 mm diameter with 1.7 mm sieve pore, the immobilized enzyme loaded on the sieve was shaken for 30 minutes, and the passage rate was calculated by measuring the weight of immobilized enzyme appeared under the sieve. The results were shown in Table 1.

When the passage rate is 100% by weight, aggregation of the immobilized enzyme is not observed, and the immobilized enzyme passes through the sieve smoothly. In such case, homogeneous packing of the immobilized enzyme into an enzyme column can be performed easily resulting the speed up of work, and consequently, the significant increase of labor efficiency may be attained by the reduction of working time.

TABLE 1

| | Example 1 | Example 2 | Example 3 | C.E.[†] 1 | C.E.[†] 2 | C.E.[†] 3 |
|---|---|---|---|---|---|---|
| Oleic acid (wt % based on the weight of the carrier) | 100 | 200 | — | — | 1000 | — |
| Rapeseed oil (wt % based on the weight of the carrier) | — | — | 100 | — | — | 1000 |
| Acetone (wt % based on the weight of the carrier) | 500 | 800 | 500 | 500 | — | — |
| Treatment temperature (° C.) | 20 | 20 | 20 | 20 | 40 | 40 |
| Treatment time (minutes) | 5 | 5 | 5 | 5 | 120 | 120 |
| Moisture content of the immobilized enzyme after treatment (wt % based on the weight of the carrier) | 7.9 | 6.5 | 7.7 | 7.2 | 134 | 30 |
| Sieve passage rate of the immobilized enzyme (% by weight) | 100 | 100 | 100 | 100 | 7 | 16 |
| Relative activity (%) | 100 | 102 | 95 | 70 | 95 | 200 |

[†]C.E.: Comparative Example

From the results shown in Table 1, the immobilized enzyme which has been treated only by fats and oils after immobilization (Comparative Example 3: C.E. 3) have maintained sufficient enzyme activity, but the moisture content of the immobilized enzyme was not small, and had the drawback in handling. Also, the immobilized enzyme which has been treated only by fatty acid after immobilization (Comparative Example 2: C.E. 2) was not reduced moisture content in the immobilized enzyme and quite difficult in handling, and the enzyme activity was slightly decreased. Further, the immobilized enzyme which has been treated only by organic solvent (Comparative Example 1: C.E. 1) was easy for handling but observed significant decrease in activity. In consequence, it is expected from the results of Comparative Examples of 1 through 3 that when the treatment with organic solvent and fatty acid is carried out at the same time, the activity decreases and handling is not improved so much.

However, the immobilized enzyme prepared according to the method of the present invention, which was contacted after immobilization with an organic solvent in which fat-soluble fatty acids or the derivatives thereof have been dissolved, had the same easiness for handling as that treated with organic solvent only, and maintained enzyme activity in high level. These results were far beyond expectation of the present inventors.

The invention claimed is:

1. A method for producing an immobilized enzyme which comprises the steps of
   i) immobilizing an enzyme used for hydrolyzing fats and oils on a immobilization carrier having a particle size of from 100 to 1000 μm in diameter and a pore size is from 10 to 150 nm by adsorption,
   ii) adjusting the moisture content of the immobilized enzyme to from 1 to 20% by weight based on the weight of said carrier by bringing said immobilized enzyme into contact with 100 to 3000% by weight based on the weight of said carrier of an organic solvent in which 10 to 200% by weight based on the weight of said carrier of fat-soluble fatty acids or derivatives thereof have been dissolved, for a contact time of from 1 to 30 minutes,
   wherein said fat-soluble fatty acid is a saturated or unsaturated fatty acid with 8 to 18 carbon atoms with a linear or a branched chain.

* * * * *